United States Patent [19]
Yule

[11] Patent Number: 5,996,576
[45] Date of Patent: Dec. 7, 1999

[54] ATOMISING NOZZLE

[75] Inventor: Andrew J. Yule, Manchester, United Kingdom

[73] Assignee: Glaxo Group Limited, United Kingdom

[21] Appl. No.: 09/043,679

[22] PCT Filed: Sep. 24, 1996

[86] PCT No.: PCT/EP96/04153

§ 371 Date: Mar. 26, 1998

§ 102(e) Date: Mar. 26, 1998

[87] PCT Pub. No.: WO97/11783

PCT Pub. Date: Apr. 3, 1997

[30] Foreign Application Priority Data

Sep. 27, 1995 [GB] United Kingdom .................... 9519692

[51] Int. Cl.$^6$ .................................................. A61G 15/00
[52] U.S. Cl. ...................... 128/203.12; 239/433
[58] Field of Search ...................... 239/433, 338, 239/350, 340, 348, 346, 8; 128/203.12, 204.18

[56] References Cited

U.S. PATENT DOCUMENTS

| | | | |
|---|---|---|---|
| 707,282 | 8/1902 | Truax | 239/338 X |
| 742,986 | 11/1903 | Hopkins | 239/338 X |
| 2,063,397 | 12/1936 | Paschall | 239/338 X |
| 2,488,988 | 11/1949 | Schmitt | 239/338 |
| 2,782,073 | 2/1957 | Shadegg | 239/338 X |
| 2,966,312 | 12/1960 | Wilson et al. | 239/338 |
| 3,018,971 | 1/1962 | Chesey | 239/338 |
| 4,344,574 | 8/1982 | Meddings et al. | 239/338 |
| 4,915,302 | 4/1990 | Kraus et al. | 239/433 X |
| 4,923,743 | 5/1990 | Stewart . | |
| 5,385,304 | 1/1995 | Haruch . | |

FOREIGN PATENT DOCUMENTS

| | | |
|---|---|---|
| 0 040 927 | 12/1981 | European Pat. Off. . |
| 0 430 359 | 6/1991 | European Pat. Off. . |
| 2 670 138 | 6/1992 | France . |
| 4306 458 | 9/1994 | Germany . |
| 4306458 | 9/1994 | Germany . |
| 1 164 790 | 9/1969 | United Kingdom . |
| 2 055 307 | 3/1981 | United Kingdom . |

*Primary Examiner*—Kevin Weldon
*Attorney, Agent, or Firm*—Nixon & Vanderhye P.C.

[57] ABSTRACT

An atomising nozzle assembly and a method for generating a respirable spray of droplets of a size suitable for medical inhalation therapy from a liquid medicament. The nozzle assembly comprises a gas nozzle (2) for producing a jet of gas and a liquid nozzle (3) for ejecting the liquid to be atomised into the jet of gas at a position downstream of the gas nozzle (2). The gas nozzle (2) and the liquid nozzle (3) are configured such that the jet of gas impinges on the liquid at an acute angle to atomise the liquid. The nozzle assembly and method can create a respirable spray using a gas/liquid mass ratio of less than 0.5.

16 Claims, 5 Drawing Sheets

ATOMISING NOZZLE

This application Ser. No. 09/043,679 is the National Stage of PCT/EP96/04153.

BACKGROUND OF THE INVENTION

1. Field of the Invention

This invention relates to atomising nozzles used for hand held sprayers such as so-called aerosols and pump type atomisers, intended for the application of liquid pharmaceutical products.

2. Description of the Related Art

Aerosol type sprayers are used throughout the world for dispensing a wide range of products, for example, hair lacquer, furniture polish, cleaners, paint, insect killers and medicaments. Until recently, chlorofluorocarbons (CFC's) were the most common of the propellant gases used in aerosols because they are inert, miscible with a wide range of products, are easily liquefied under low pressures, give a substantially constant product flow-rate, and can produce sprays of droplets having mean diameters in the range of 3 to over 100 micrometers. However, in the 1970's it was confirmed that CFC's were probably responsible for depleting the Earth's protective ozone layer, and in 1987, most countries signed the Montreal Protocol to phase out the use of CFC's and have since agreed to stop use of CFC's for non-essential applications by the end of 1995. One notable exemption to this deadline for cessation of use is in relation to metered dose inhalers (MDI's) for medicaments, which are regarded as an essential use of CFC's, but even this use of CFC's will eventually be phased out.

Gases such as air and nitrogen have the advantages of causing no environmental damage, being non-flammable and causing no ill effects if inhaled. Such gases can be used to propel liquid from a canister, but with a simple orifice or a swirl orifice very high pressures are required to produce a fine spray suitable for an MDI.

Other types of aerosol generators for delivery of liquid pharmaceutical products exist for research and hospital applications, such as nebulisers. However, these generally contain baffles to remove larger droplets and use high air flowrates so making them unsuitable for use in portable, convenient atomisers.

It is also possible to force liquid at high pressure through a very small hole (5–10 micrometers diameter) to produce droplets of about 5 micrometers diameter, but these methods are unsuitable or uneconomic for large scale manufacture, mainly because of the difficulty in making very small holes in a suitable material, and, to prevent blockage of the hole, the need for exceptional cleanliness in the manufacture of the parts, together with ultrafiltration of the fluid to be sprayed.

Many of the drugs used in the treatment of respiratory disorders are insoluble in vehicles such as water and are dispensed as suspensions. The drug particles are produced in a respirable size of 1–5 micrometers. Particles of this size tend to block the very small holes (5–10 micrometers) used by known devices.

For veterinary and some human vaccination applications, high pressure (125–500 bars) spring or gas operated pumps (so-called needle-less injectors) are in common use to inject a jet of drug through the skin ("intra-dermal injection") without the use of needles, and attachments are available to convert the jet to a spray for administering drugs to the nasal passages of large animals such as swine. However, the smallest droplet size obtainable is in the order of 40 micrometers, and the range of applications for these injectors is limited.

Compressed air atomisers such as air brushes and commercial paint sprayers consume large quantities of air, and to obtain droplets of 5 micrometers with water for example, a gas to liquid mass ratio of over 36:1 is required which is impractical for convenient, portable sprayers.

Spray nozzles in which a liquid is atomised by impingement of multiple jets of fluid on each other, e.g. air and liquid jets, are known. U.S. Pat. No. 5,385,304 describes an air assisted atomising spray nozzle in which a jet of liquid is atomised within a mixing chamber by the shearing action of several jets of air directed in substantially perpendicular relation to the liquid jet. The nozzle may be used to deliver liquid in a finely atomised state and suitable applications include use for the delivery of agricultural chemicals and pesticides, humidifying systems and scrubbing systems for coal furnaces. The nozzle described is believed to provide a high air efficiency by the use of an opposing cross-flow of air and the air/liquid mass ratio of the embodiment described is from 0.13 to 0.27. Although the spray particle size is not defined, the nozzle is described as producing a fine liquid droplet spray, and the applications discussed suggest that it might produce droplet sizes down to a minimum of 50 micrometers in diameter.

For MDI's used for treating certain respiratory disorders it is essential that the aerodynamic particle size should be less than 15 micrometers, preferably less than 10 micrometers, so that the droplets are able to penetrate and deposit in the tracheobronchial and alveolar regions of the lung. For a spray composed of droplets with a range of sizes, more than 5% by weight of the droplets should have an aerodynamic diameter less than 6.4 micrometers, preferably more than 20% by weight of the particles have an aerodynamic diameter less than 6.4 micrometers.

Inhalers may also be designed to deliver drugs to the alveolar sacs of the lung to provide a route for adsorption into the blood stream of drugs that are poorly adsorbed from the alimentary tract. To reach the alveoli it is essential that the aerodynamic diameter of the particles is less than 10 micrometers, preferably 0.5–5 micrometers Current thinking suggests that to create smaller spray droplets from impinging fluid nozzles it is necessary to increase the gas/liquid mass ratio (GLR) resulting in an associated increase in gas reservoir size required to deliver the necessary mass of propellant. However, for the application of such technology to portable hand held inhalation devices, it is desirable for the GLR to be small to limit the size of reservoir required. The alternative of using hand or finger driven, or primed pumps to meter and produce the liquid and gas flows also requires that the volume and pressure of gas required are minimised to allow a small pump size and to minimise the effort required by the patient.

SUMMARY OF THE INVENTION

The present invention aims to provide a design of atomising nozzle assembly suitable for use in a hand held inhalation device and which is capable of being used to produce a spray of droplets of a size suitable for inhalation, without the use of conventional liquefied gas propellants.

According to the present invention there is provided an atomising nozzle assembly for generating a respirable spray of droplets of a size suitable for medical inhalation therapy from a liquid medicament, the nozzle assembly comprising a gas nozzle for producing a jet of gas and a liquid nozzle for ejecting the liquid to be atomised into the jet of gas at a position downstream of the gas nozzle, wherein the gas nozzle and the liquid nozzle are configured such that the jet of gas impinges on the liquid at an acute angle to atomise the liquid.

The present invention further provides an atomising nozzle assembly comprising at least one nozzle for ejecting the liquid to be atomised and at least one nozzle for producing a jet of gas, the at least one liquid nozzle and the at least one gas nozzle being configured such that the liquid is impacted upon by the gas jet so as to produce a respirable spray of droplets of a size suitable for medical inhalation therapy, the gas to liquid mass flowrate ratio being less than 0.5.

By use of a gas and liquid nozzle configuration wherein the jet of gas impinges on the liquid at an acute angle it is possible to create a respirable spray with a GLR less than 0.5.

Preferably the gas to liquid mass ratio is 0.2 or less.

Suitably, the gas nozzle is at least partially obscured by the liquid nozzle such that the liquid is delivered from the liquid nozzle directly into the jet of gas.

Preferably the liquid nozzle is bevelled.

Suitably, the liquid and gas nozzles have an outlet diameter between 50 micrometers and 200 micrometers.

The liquid and gas nozzles are suitably configured to give a fluid impingement angle of between 30° and 90°. Preferably the liquid and gas nozzles are configured to give a fluid impingement angle of between 40° and 60°.

Suitably, the liquid nozzle outlet is positioned up to 10 gas nozzle outlet diameters downstream of the gas nozzle outlet. Preferably the liquid nozzle outlet is positioned between 1 and 4 gas nozzle outlet diameters downstream of the gas nozzle outlet.

In a further aspect of the present invention there is provided a method for generating a respirable spray of droplets of a size suitable for medical inhalation therapy from a liquid medicament by introducing the said liquid into a jet of gas, wherein the jet of gas impinges on the liquid at an acute angle to the direction of flow of the liquid.

The present invention also provides a method for creating a respirable spray of droplets of a size suitable for medical inhalation therapy from a liquid medicament by introducing the said liquid into a jet of gas such that the said liquid is impacted upon by the said jet of gas, the gas to liquid mass flowrate ratio being less than 0.5.

Preferably the gas to liquid mass flowrate ratio is 0.2 or less.

In a preferred embodiment the shapes and sizes of the liquid and gas supply nozzles are chosen to maximise the inhalable proportion of the spray whilst minimising the amount of gaseous propellant required. This requires that the liquid ejection nozzle has a shape and position that disturbs the gas jet in such a manner that the break-up of the liquid occurs throughout the cross section of the gas flow and, in particular, in regions of high gas velocity, and that turbulence, vortex formation and shock wave production created by interaction of the gas jet with the liquid nozzle act to improve break-up into small droplets and the dispersion of droplets across the gas jet.

The invention will now be described with reference to the accompanying drawings, in which:

DETAILED DESCRIPTION OF THE INVENTION

Figure 1A:
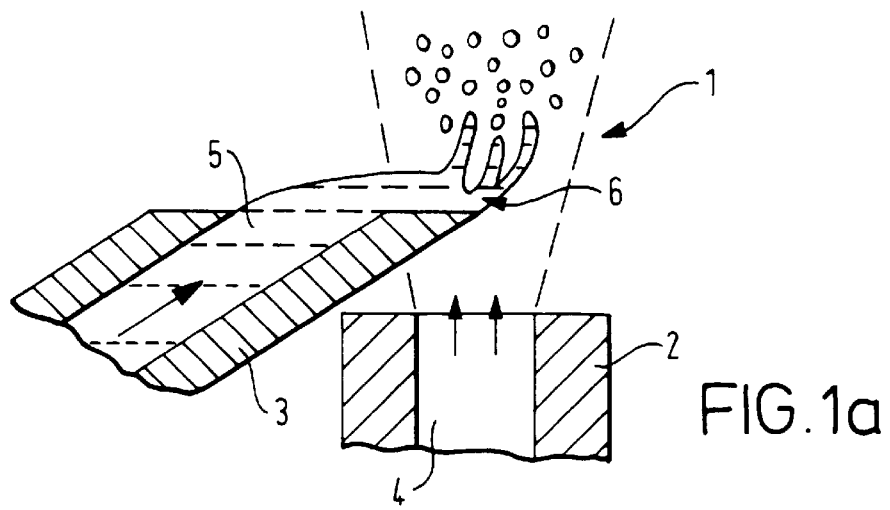
FIGS. 1a, 1b, 1c and 1d are section, end and schematic views showing a liquid and gas nozzle configuration according to the invention.

Referring to FIGS. 1a, 1b, 1c and 1d, a preferred form of the atomising nozzle assembly 1 consists of a cylindrical gas nozzle 2 having a circular orifice of 125 microns internal diameter, and a bevelled liquid nozzle 3 of a similar internal diameter but presenting an eliptical outlet orifice positioned partly in front of gas nozzle 2. Liquid nozzle 3 is arranged such that the liquid outlet orifice is positioned approximately 1 gas outlet orifice diameter downstream of the gas outlet orifice. The lateral position of liquid nozzle 3 relative to gas nozzle 2 may be expressed as percentage obscuration of the gas nozzle and is determined according to FIG. 1c by the equation:

$$L = 100 \ r/D (\%).$$

The liquid and gas nozzles may be made from stainless steel hypodermic 316 or any other suitable material. Gas nozzle 2 and liquid nozzle 3 define an acute angle of 40° between them.

In use, air 4 is delivered at sonic velocity through gas nozzle 2 and liquid 5 under pressure is introduced into the gas jet at a velocity around 1.4 m/s through liquid nozzle 3. For the purposes of the experimental results given below the liquid used is water. However, the liquid may, for example, consist of an aqueous suspension or solution of a medicament or other bioactive molecule. Bioactive molecules suitable for this purpose include proteins, peptides, oligonucleosides and genes such as DNA complexed with an appropriate lipid carrier, for example, DNA encoding cystic fibrosis transmembrane conductance regulator (CFTR) protein/cationic lipid complex, useful for the treatment of cystic fibrosis.

Medicaments suitable for this purpose are, for example for the treatment of respiratory disorders such as asthma, bronchitis, chronic obstructive pulmonary diseases and chest infections. Additional medicaments may be selected from any other suitable drug useful in inhalation therapy and which may be presented as an aqueous suspension or solution. Appropriate medicaments may thus be selected from, for example, analgesics, e.g. codeine, dihydromorphine, ergotamine, fentanyl or morphine; anginal preparations, e.g. diltiazem; antiallergics, e.g. cromoglycate, ketotifen or neodocromil; antiinfectives e.g. cephalosporins, penicillins, streptomycin, sulphonamides, tetracyclines and pentamidine; antihistamines, e.g. methapyrilene anti-inflammatories, e.g. fluticasone, flunisolide, budesonide, tipredane or triamcinolone acetonide; antitussives, e.g. noscapine; bronchodilators, e.g. salmeterol, salbutamol, ephedrine, adrenaline, fenoterol, formoterol, isoprenaline, metaproterenol, phenylephrine, phenylpropanolamine, pirbuterol, reproterol, rimiterol, terbutaline, isoetharine, tulobuterol orciprenaline, or (−)-4- amino-3,5-dichloro-α-[[[6-[2-(2-pyridinyl)ethoxy]hexyl]amino]methyl]benzenemethanol; diuretics, e.g. amiloride; anticholinergics e.g. ipratropium, atropine or oxitropium; hormones, e.g. cortisone, hydrocortisone or prednisolone; xanthines e.g. aminophylline, choline theophyllinate, lysine theophyllinate or theophylline and therapeutic proteins and peptides, e.g. insulin or glucagon. It will be clear to a person skilled in the art that, where appropriate, the medicaments may be used in the form of salts (e.g. as alkali metal or amine salts or as acid addition salts) or as esters (e.g. lower alkyl esters) or as solvates (e.g. hydrates) to optimise the activity and/or stability of the medicament. Preferred medicaments are salbutamol, salbutamol sulphate, salmeterol, salmeterol xinafoate, fluticasone propionate, beclomethasone dipropionate and terbutaline sulphate. It is to be understood that the suspension or solution of medicament may consist purely of one or more active ingredients.

The shape and position of the liquid nozzle 3 causes interaction with the air jet such that the liquid flows mainly to the tip 6 of the nozzle and detaches and rapidly atomises in the high velocity gas zone to form a slow moving spray. Slow moving sprays are particularly suitable for delivery to the tracheobronchial and alveolar regions of the lung as they reduce the amount of impingement of droplets at the back of the throat which tends to result from faster moving sprays. Slow moving sprays are also beneficial to the user by facilitating coordination of actuation of the device with the act of inhalation. The size of the droplets is controlled, inter alia, by the respective gas and liquid flowrates, and the shapes of both nozzles. The positioning of liquid nozzle 3 in front of gas nozzle 2 creates turbulence, vortex shedding and shock wave formation in the jet of air which is beneficial to atomisation of the liquid 5, and as described with reference to FIG. 2a below, it has been found that use of a bevelled orifice rather than a square edge orifice allows increased flexibility with respect to the lateral position of the liquid nozzle relative to the gas nozzle, so relaxing the tolerances required during manufacture.

Figure 1B:
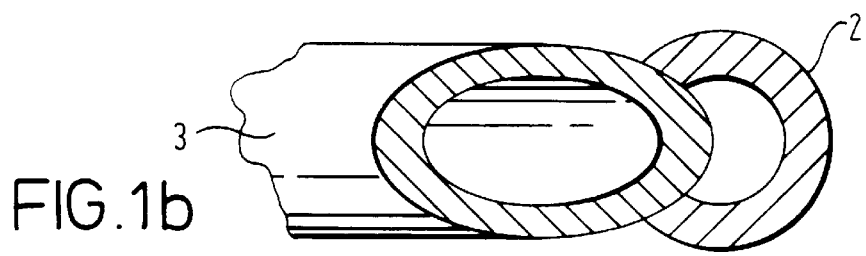
Figure 1C:
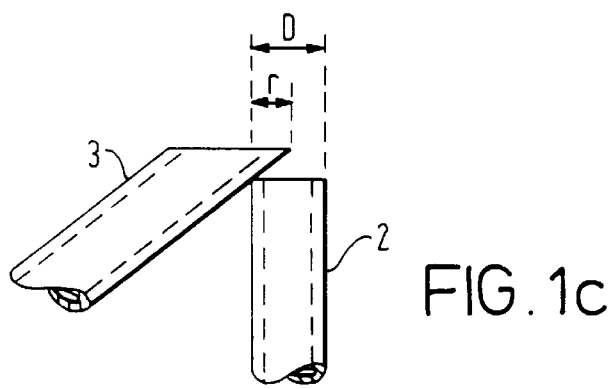
Figure 1D:
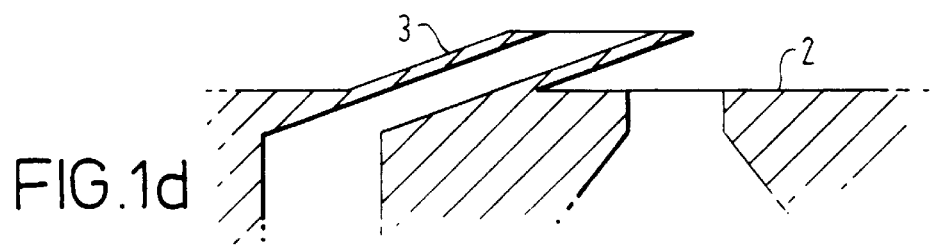

FIG. 1d shows how liquid and gas nozzles might be incorporated into a single moulded component. The nozzles themselves might be manufactured by laser drilling or by injection moulding with or without hypodermic capillary inserts.

Figure 2A:
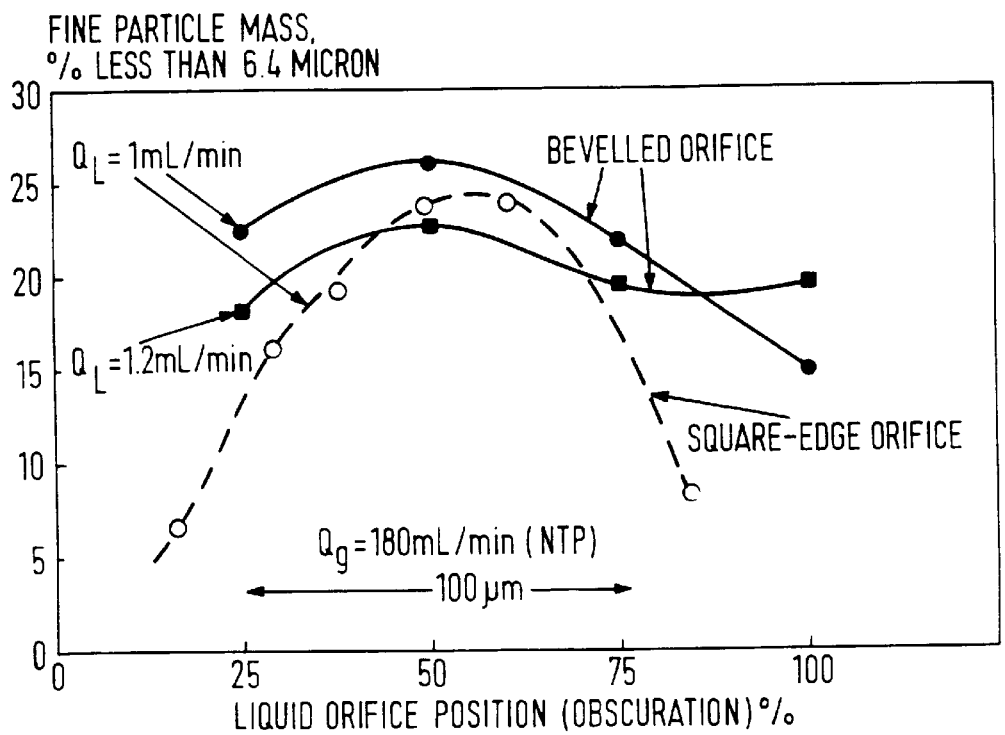
FIGS. 2a, 2b, 2c and 2d are graphs showing the percentage by mass of drops less than 6.4 micrometers in diameter created with varying parameters relating to the liquid and gas nozzles as shown in FIGS. 1a, 1b and 1c.

FIG. 2a demonstrates the results of tests carried out on one atomising nozzle with a bevelled liquid orifice as described above and one atomising nozzle with a square edge liquid orifice using different liquid flowrates but constant gas flowrate to determine how the lateral position of the liquid nozzle relative to the gas nozzle (percentage obscuration) affects the percentage of fine particle mass created; that is droplets with a diameter less than 6.4 micrometers as measured by the deposition of spray in the second stage of a twin impinger device. It is evident from FIG. 2a that the optimum results at liquid flowrates of 1.0 ml/min and 1.2 ml/min are obtained at approximately 50% obscuration, though the deterioration of spray characteristics with different obscuration values is much less marked with the bevelled orifice than with the square edge orifice.

Figure 2B:
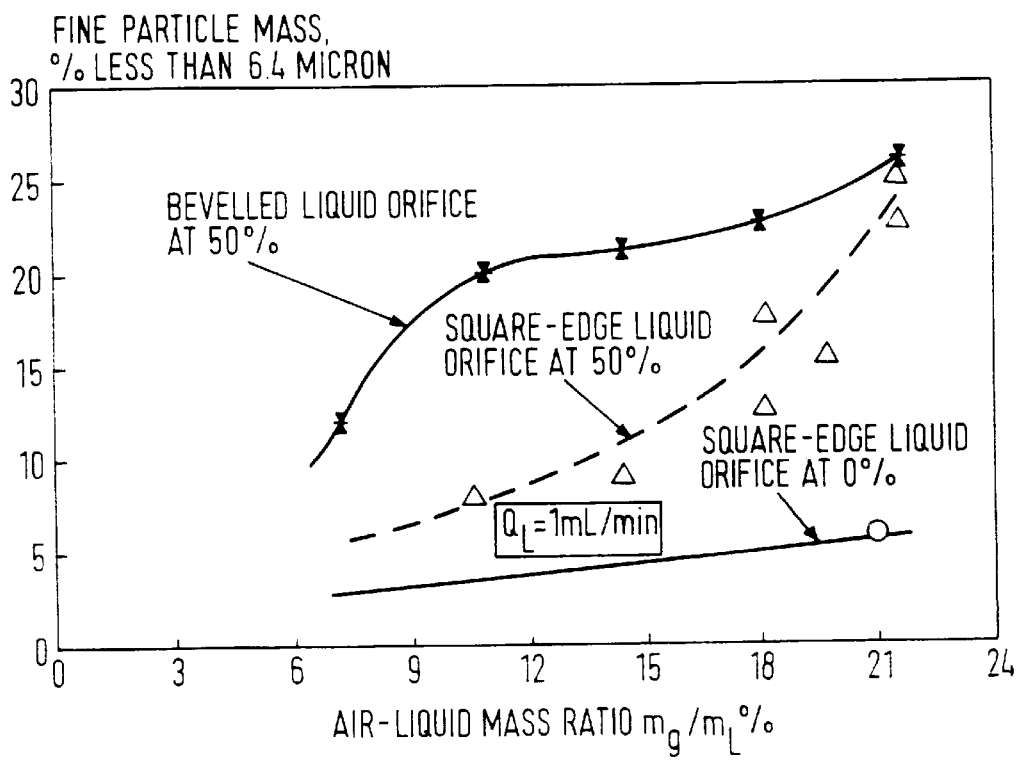

FIG. 2b shows the variation in fine particle mass creation with variation in GLR for one atomising nozzle with a bevelled liquid orifice and one atomising nozzle with a square edge liquid orifice using different percentage obscurations with constant liquid flowrate. This demonstrates that a significant improvement in atomisation efficiency is obtained using the bevelled liquid orifice with over 20% fine particle mass being attained with a GLR of around 0.12.

Figure 2C:
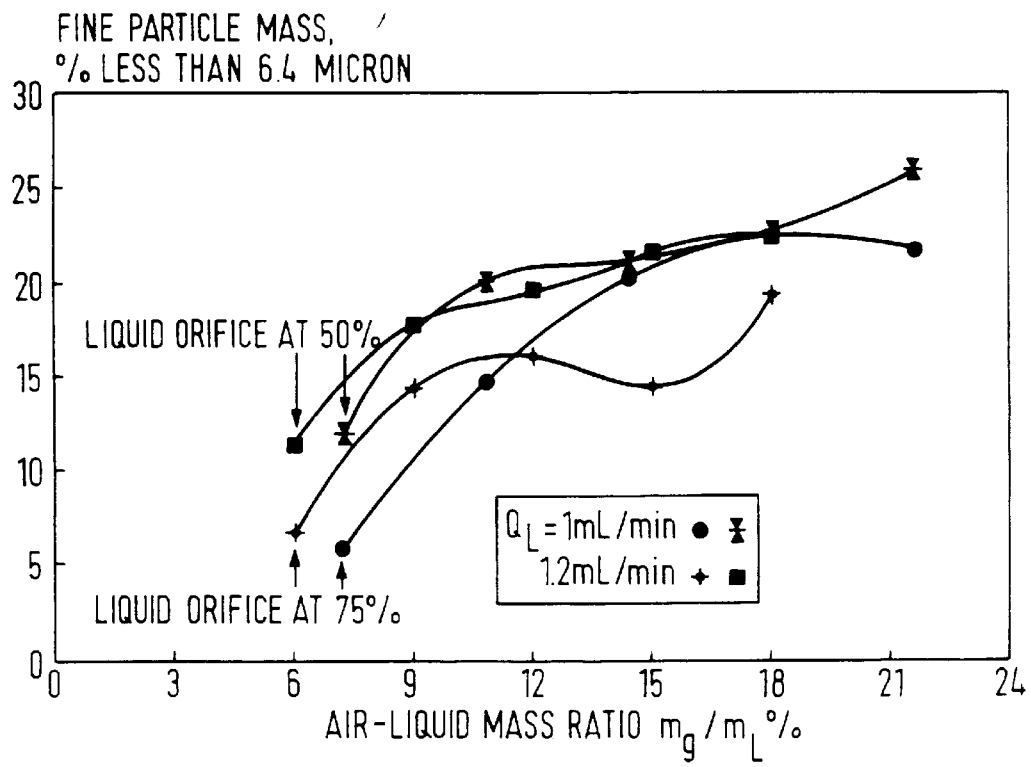

FIG. 2c shows the variation in fine particle mass created with variation in GLR at selected liquid flowrates and gas nozzle obscurations using a bevelled liquid nozzle. This figure demonstrates that improved performance results from increased GLR and that 20% deposition is achieveable at a GLR of around 0.12 with 50% obscuration.

Figure 2D:
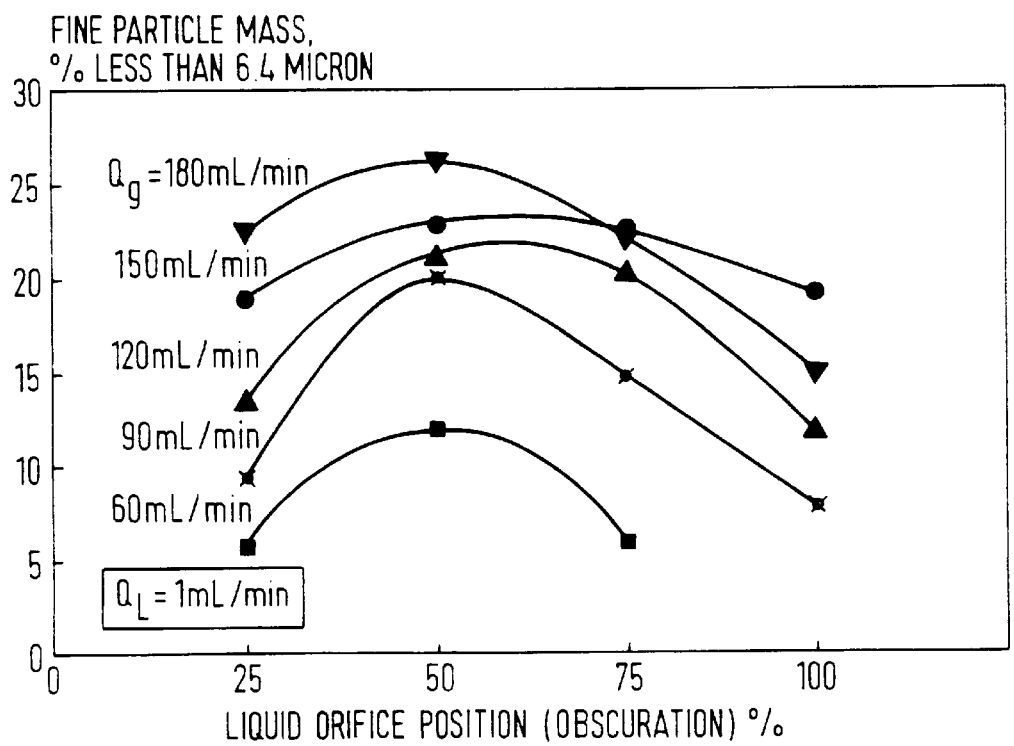

FIG. 2d shows the optimum gas nozzle obscuration for different gas flowrates using a constant liquid flowrate of 1.0 ml/min. For manufacturing purposes it is desirable to be able to achieve the required spray characteristics over a range of liquid orifice positions in order to allow for manufacturing inaccuracies. This also aids the achievement of consistent performance throughout the lifetime of the nozzle. From FIG. 2d it is clear that for the creation of 20% of droplets with a diameter less than 6.4 micrometers, gas flowrates of 120 ml/min and above will allow for some tolerance on obscuration.

Increasing the liquid flowrate allows the gas flowrate to be increased proportionately to maintain the same GLR, and similar trends to those shown in FIG. 2d are found, but with optimum spray characteristics occurring at higher obscurations. Using 125 micrometer diameter nozzles and GLR values of 0.2, liquid flowrates of 1.2 ml/min and 1.8 ml/min exhibit optimum obscurations of 50±5% and 75±5% respectively.

Figure 3A:
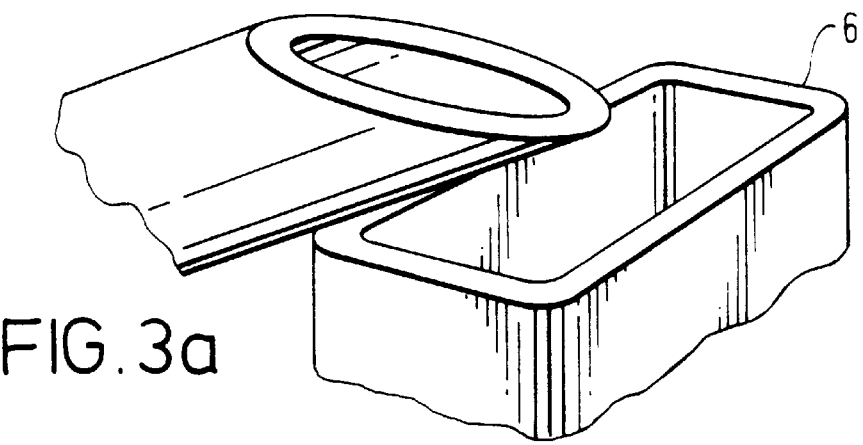
FIGS. 3a, 3b and 3c are perspective and sectional views showing alternative shapes and arrangements of liquid and gas nozzle configurations according to the invention.

FIG. 3a shows an alternative nozzle assembly design which is similar to that shown in FIGS. 1a–1c but in which the gas nozzle 6 has a rectangular profile. Such a gas nozzle profile may reduce the chance of the liquid jet 'punching' through the gas jet leading to non atomisation or partial atomisation. By suitable design of the gas and liquid nozzles it may be possible to increase atomisation efficiency through increased gas vortex shedding around the liquid nozzle outlet.

Figure 3B:
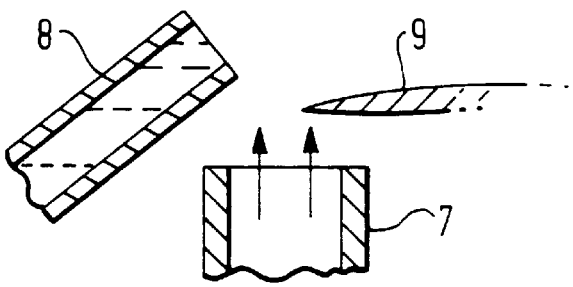

FIG. 3b shows another nozzle assembly in which the gas nozzle 7 has a profile similar to that depicted in FIGS. 1a to 1c, and the liquid nozzle 8 presents a 'square edge' circular orifice. A blade 9 is positioned partly in front of gas nozzle 7, and this helps to generate turbulence, vortex shedding and shock waves in the gas jet to aid atomisation and dispersion of liquid. Blade 9 may additionally be made to vibrate to enhance its effect.

Figure 3C:
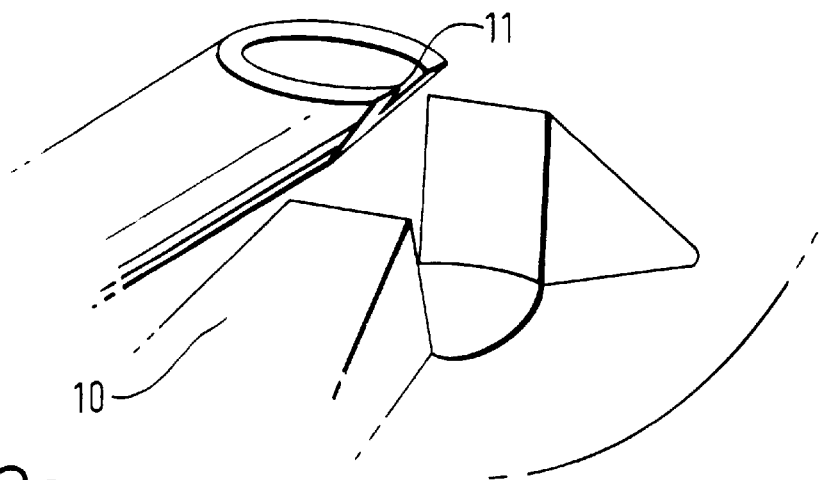

FIG. 3c shows a further nozzle assembly in which the gas nozzle incorporates side wall extensions 10 and the liquid nozzle has a cut away section 11 to enhance the spray shape and liquid-gas mixing.

Figure 4:
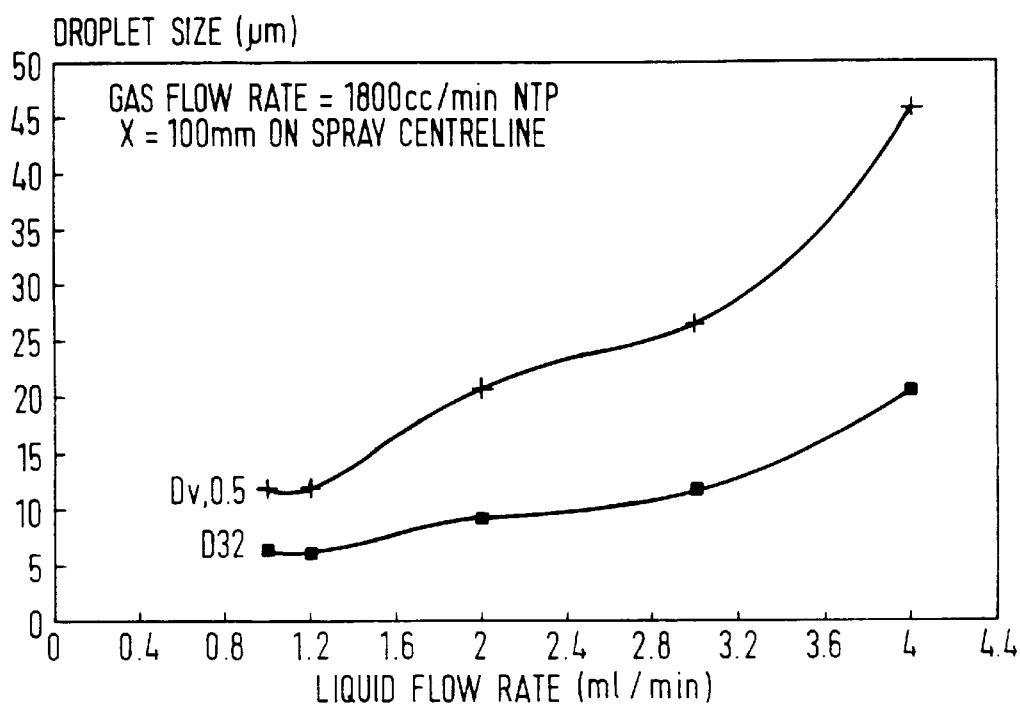
FIG. 4 is a graph showing average drop sizes produced by a nozzle according to the invention with varying liquid flowrates.

FIG. 4 shows the average drop size produced by an atomiser using two 125 micrometer diameter nozzles with a bevelled liquid outlet orifice. Two methods of defining mean drop diameter are used; $D_v,0.5$ is the volume median diameter and $D_{32}$ is the Sauter mean diameter. Measurements were made using a Malvern ST2600 laser diffraction instrument at a position 100 mm downstream from the liquid nozzle. The results show that for a constant atomising air flow rate the drop size increases as the liquid flow rate is increased. However, the full drop size distributions for liquid flow rates of 1.0 ml/min and 1.2 ml/min show that 21.3% by mass of droplets produced are smaller than 6.3 micrometers diameter, and this is sufficient to render satisfactory operating conditions for an MDI.

Figure 5:
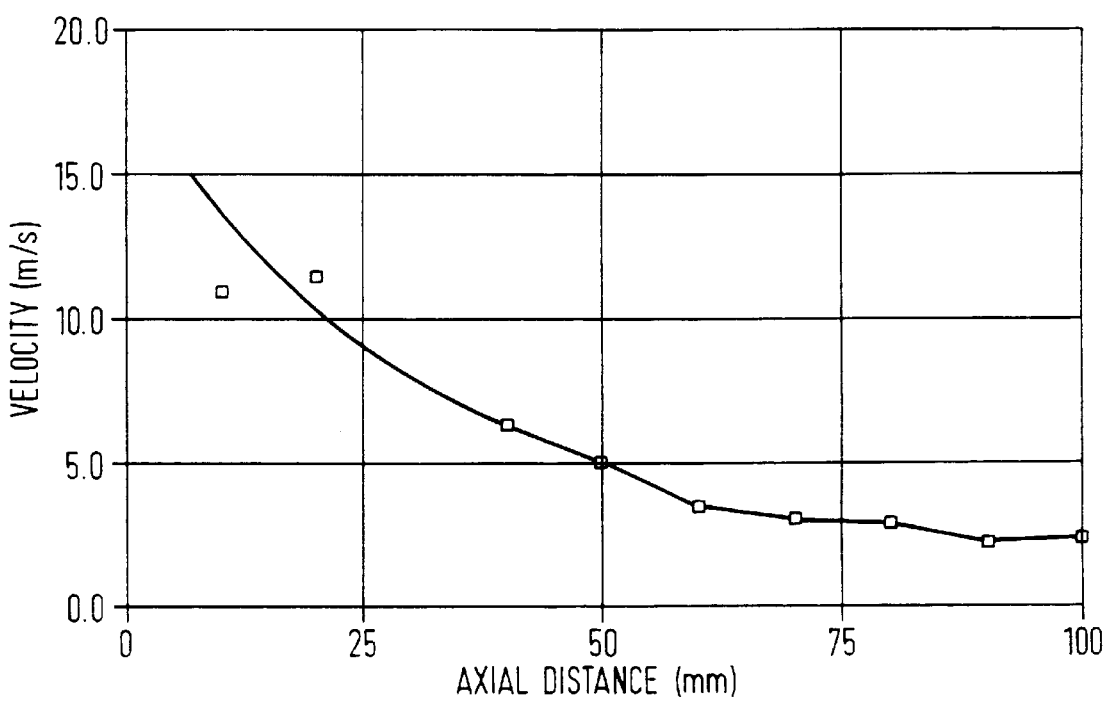
FIG. 5 is a graph showing mean drop velocities produced by a nozzle according to the invention.

FIG. 5 shows the mean drop velocity at axial distances from the liquid nozzle along the centre line of a spray produced by an atomiser using two 125 micrometer diameter nozzles at 40° with a gas flowrate of 180 ml/min. Measurements were made using a Dantec phase doppler anemometer. The drop velocities exhibited are less than those delivered by conventional propellant based MDIs. Such reduced drop velocity leads to lower deposition in the oropharnygeal region when sprayed into the mouth for delivery of drug to the respiratory tract. Such characteristics may provide a distinct advantage over conventional propellant based MDI delivery by leading to a reduction in local effects and systemic exposure due to oral absorption.

It will be appreciated that an atomising device may comprise a plurality of atomising nozzle assemblies as described arranged in an array.

I claim:

1. An atomising nozzle assembly comprising at least one nozzle having an outlet orifice for ejecting a liquid medicament to be atomised and at least one nozzle having an outlet orifice for producing a jet of gas, the at least one liquid nozzle and the at least one gas nozzle being configured such that the liquid medicament is impacted upon by the gas jet so as to produce a respirable spray of droplets of a size suitable for medical inhalation therapy, wherein the liquid is delivered under pressure to provide a gas to liquid mass flow rate ratio of less than 0.5.

2. An atomising nozzle assembly according to claim 1, characterised in that the gas to liquid mass ratio is 0.2 or less.

3. An atomising nozzle assembly according to claim 1, characterised in that the gas nozzle and the liquid nozzle are configured such that the jet of gas impinges on the liquid at an acute angle to atomise the liquid.

4. An atomising nozzle according to claim 1, characterised in that the gas nozzle is at least partially obscured by the liquid nozzle such that the liquid is delivered from the liquid nozzle directly into the jet of gas.

5. An atomising nozzle assembly according to claim 1, characterised in that the liquid nozzle is bevelled such that the plane of the outlet orifice is approximately parallel to the plane of the outlet orifice of the gas nozzle.

6. An atomising nozzle assembly according to claim 1, characterised in that the liquid and gas nozzles have an outlet diameter between 50 micrometers and 200 micrometers.

7. An atomising nozzle assembly according to claim 1, characterised in that the gas nozzle and liquid nozzle are configured such that the jet of gas impinges on the liquid at an angle of between 40° and 60°.

8. An atomising nozzle assembly according to claim 1, characterised in that the liquid nozzle outlet is positioned up to 10 gas nozzle outlet diameters downstream of the gas nozzle outlet.

9. An atomising nozzle assembly according to claim 8, characterised in that the liquid nozzle outlet is positioned between 1 and 4 gas nozzle outlet diameters downstream of the gas nozzle outlet.

10. An atomising nozzle comprising a plurality of atomising nozzle assemblies according to claim 1 arranged in any array.

11. A method for creating a respirable spray of droplets of a size suitable for medical inhalation therapy from a liquid medicament by introducing the liquid medicament under pressure into a jet of gas such that the liquid is impacted upon by the said jet of gas, the gas to liquid mass flowrate ratio being less than 0.5.

12. A method according to claim 11, characterised in that the gas to liquid mass flowrate ratio is 0.2 or less.

13. A method according to claim 11, characterised in that the jet of gas impinges on the liquid at an acute angle to the direction of flow of the liquid.

14. A method according to claim 11, characterised in that the liquid is introduced into the jet of gas by means of a nozzle which is at least partially positioned within the jet of gas.

15. A method according to claim 11, characterised in that the liquid is introduced into the jet of gas by means of a nozzle having an outlet diameter between 50 micrometers and 200 micrometers.

16. A method according to claim 13, characterised in that the gas impinges on the liquid at an angle of between 40° and 60°.

* * * * *